United States Patent [19]

Ambler et al.

[11] Patent Number: 5,514,706
[45] Date of Patent: May 7, 1996

[54] PHARMACEUTICAL COMPOUNDS

[75] Inventors: Samantha J. Ambler, Camberley, England; William F. Heath, Jr., Indianapolis; Jai P. Singh, Carmel, both of Ind.; Colin W. Smith, Bracknell, England; Lawrence E. Stramm, Indianapolis, Ind.

[73] Assignee: Eli Lilly and Company, Indianapolis, Ind.

[21] Appl. No.: 342,993

[22] Filed: Nov. 21, 1994

Related U.S. Application Data

[63] Continuation of Ser. No. 45,396, Apr. 9, 1993, abandoned.

[51] Int. Cl.$^6$ .................... A61K 31/35; A61K 31/40; A61K 31/435
[52] U.S. Cl. .................... 514/454; 514/422; 514/320; 514/212; 549/389; 548/525; 546/196; 540/485
[58] Field of Search .................... 514/454, 422, 514/320, 212; 549/389; 548/525; 546/196; 540/485

[56] References Cited

U.S. PATENT DOCUMENTS 4,225,722  9/1980  Connor et al. .................... 548/253

FOREIGN PATENT DOCUMENTS

WOA91/19707  12/1991  WIPO.

OTHER PUBLICATIONS

Elagamey, et al. *Chemical Abstracts*, 118: 233918a, (Jun. 7, 1993)
Atalla, et al., *Chemical Abstracts*, 115: 49458a (Aug. 5, 1991).
Elagamy, et al., *Collect. Czech. Chem. Commun.*, 55: 524–534 (1990).
Koester, et al., *Chemical Abstracts*, 108:5822c, (Jan. 4, 1988).
Vlahos, et al., *The Journal of Biological Chemistry*, 269:7, 5241–5248 (Feb./1994).
Elnagdi, et al., *Naturfoschung B*, 47(4), pp. 572–578 (1992).
Elagamey, et al. *Indian Journal of Chemistry*, 29B, 885–886 (1990).
Elagamey, et al., *Collection Czechoslovak Chem. Commun.* 53(7), 1534–1538 (1988).
Otto, et al., *Monatshefte für Chemi*, 110, 115–119 (1979).
Otto, et al., *Monatshefte für Chemi*, 110, 249–256 (1979).
Otto, et al., *Arch. Pharm.*, 312(6), 548–550 (1979).
Abdel–Latif, *Indian Journal of Chemistry*, 29B, 664–666 (1990).
Sharanin, et al., *Zhurnal Organicheskoi Khimii*, 18, 9, 2003–2005 (1982).
Klokol, et al., *Zhurnal Organicheskoi Khimii*, 23, 2, 412–421 (1987).

*Primary Examiner*—Nicky Chan
*Attorney, Agent, or Firm*—Daniel W. Collins; Steven P. Caltrider; David E. Boone

[57] ABSTRACT

This invention provides novel compounds and pharmaceutical methods comprising the administration of a compound of the Formula I:

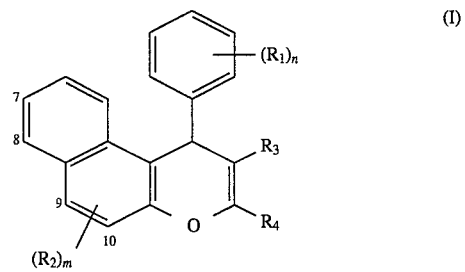

wherein n, m, $R_1$, $R_2$, $R_3$ and $R_4$ are variables.

4 Claims, No Drawings

PHARMACEUTICAL COMPOUNDS

This application is a continuation of U.S. application Ser. No. 08/045,396, filed on Apr. 9, 1993, now abandoned.

BACKGROUND OF THE INVENTION

The compounds of the present invention have an antiproliferative effect on cell division and are thus indicated for use in the treatment of diseases where excess cell proliferation or protease release is an important aspect of the pathology. Therefore, the compounds are useful in treating diabetic complications and restenosis.

Diabetic complications, including diabetic retinopathy, nephropathy, and neuropathy are largely the result of abnormalities in microvascular function. Changes in vascular function include increased blood vessel permeability and altered blood flow. These changes precede the development of the clinical symptoms of diabetic complications.

The later stages of diabetic retinopathy and proliferative vitreoretinopathy are characterized by the growth of new blood vessels, or angiogenesis. One of the early events in angiogenesis is secretion of proteases involved in the dissolution of the basement membrane. These proteases include the plasminogen activators, procollagenase and prostromelysin. Plasminogen activators such as urokinase (uPA) and tissue plasminogen activator (tPA) are serine proteases which cleave the zymogen plasminogen to generate the active serine protease plasmin. Plasmin can influence basement membrane integrity directly through cleavage of basement membrane components or indirectly through cleavage of procollagenase and prostromelysin to generate active collagenase and stromelysin. The resulting dissolution of the basement membrane allows the endothelial cells to escape from the microvessel and begin the neovascularization process.

Increased plasmin formation also has several ramifications in terms of the permeability of the diabetic microvessel. Plasmin can directly degrade basement membrane components or can activate stromelysin, thus directly or indirectly influencing the normal turnover of heparin sulfate proteoglycan (HSPG). Because HSPG is involved in blood vessel permeability as well as growth control, this enhanced degradation of HSPG may result in its depletion from the membrane with resultant increased vessel permeability.

Microvascular dysfunctions arise through this abnormal activation of endothelial cells which is mediated, in part, through protein kinase C (PKC)-regulated pathways. See MacGregor, et al., *J Clin Invest*, 83:90–94 (1988); Lee, et al., *Proc. Natl. Acad. Sci.*, 86:5141–5145 (1989).

Agents that block or reverse the activation of endothelial cells and inhibit the alterations in microvessel function will have a beneficial effect in terms of preserving normal structure and function in the tissues affected by the complications of diabetes. The agents will improve the quality of life and longevity of diabetics.

Restenosis remains a major long term complication following surgical intervention of blocked arteries by percutaneous transluminal coronary angioplasty (PTCA), atherectomy, laser angioplasty and arterial bypass graft surgery. In about 35% of the patients who undergo PTCA, reocclusion occurs within three to six months after the procedure. The current strategies for treating vascular restenosis include mechanical intervention by devices such as stents or pharmacologic therapies including heparin, low molecular weight heparin, coumarin, aspirin, fish oil, calcium antagonist, steroids, and prostacyclin. These strategies have failed to curb the reocclusion rate and have been ineffective for the treatment and prevention of vascular restenosis. See "Prevention of Restenosis after Percutaneous Transluminal Coronary Angioplasty: The Search for a 'Magic Bullet'," Hermans et al., *American Heart Journal* 122:171–187 (July 1991).

Restenosis is characterized by the migration and proliferation of smooth muscle cells in response to injury. Agents that inhibit the proliferation of smooth muscle are useful in the treatment and prevention of restenosis.

The present invention discloses compounds useful in treating diseases in mammals where excess cell proliferation is an important aspect of the pathology. Accordingly, the present invention provides compounds of the Formula I:

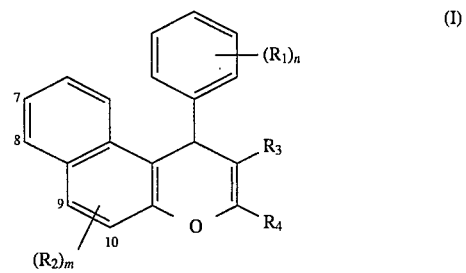

This invention further provides the use of these compounds in the treatment of diabetic complications and restenosis.

SUMMARY OF THE INVENTION

This invention provides a method of treating an immune disease or a disease in which excess cell proliferation or protease release occur, which comprises administering to a patient in need of treatment an effective amount of a compound of the Formula I:

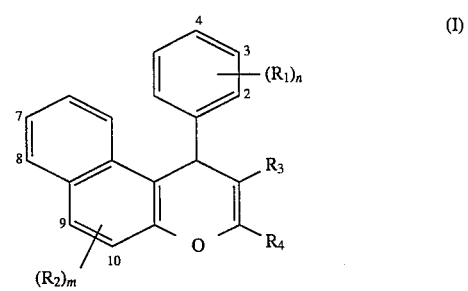

wherein n and m are independently 0, 1 or 2;

$R_1$ is halo, trifluoromethyl, $C_1$–$C_4$ alkoxy, hydroxy, nitro, $C_1$–$C_4$ alkyl, $C_1$–$C_4$ alkylthio, hydroxy-$C_1$–$C_4$ alkyl, hydroxy-$C_1$–$C_4$ alkoxy, trifluoromethoxy, carboxy, —COORS where $R_5$ is an ester group, —$COR_6$, —$CONR_6R_7$ or —$NR_6R_7$ where $R_6$ and $R_7$ are each hydrogen or $C_1$–$C_4$ alkyl;

$R_2$ is halo, trifluoromethyl, $C_1$–$C_4$ alkoxy, hydroxy, nitro, $C_1$–$C_4$ alkyl, $C_1$–$C_4$ alkylthio, hydroxy-$C_1$–$C_4$ alkyl, hydroxy-$C_1$–$C_4$ alkoxy, trifluoromethoxy, carboxy, —COORS where $R_8$ is an ester group, —$COR_9$, —$CONR_9R_{10}$ or —$NR_9R_{10}$ where $R_9$ and $R_{10}$ are each hydrogen or $C_1$–$C_4$ alkyl;

$R_3$ is nitrile, carboxy or —$COOR_{11}$ where $R_{11}$ is an ester group; and $R_4$ is $-NR_{12}R_{13}$, $-NR_{12}COR_{13}$, $-N(COR_{12})_2$, $-N=CHOCH_2R_{12}$,

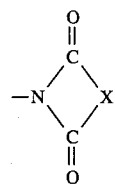

or optionally substituted 1-pyrrolyl; wherein $R_{12}$ and $R_{13}$ are each hydrogen or $C_1-C_4$ alkyl, and X is $C_2-C_4$ alkylene; and salts thereof.

Accordingly, this invention also provides a method of treating diabetic complications, which comprises administering to a patient in need of treatment an effective amount of a compound of the Formula I.

This invention further provides a method of treating restenosis which comprises administering to a patient in need of treatment an effective amount of a compound of the Formula I.

Also provided are pharmaceutical formulations comprising a compound of the Formula I and one or more pharmaceutically acceptable carriers, diluents, or excipients therefor.

The above compounds are novel with the following exceptions. Therefore, this invention further provides compounds of formula (I) above, provided that i) when m is 0, $R_3$ is nitrile and $R_4$ is $-NH_2$, n is not 0 and $-(R_1)_n$ is not 2-fluoro, 2-chloro, 2-methoxy, 3-fluoro, 3-nitro, 4-methyl, 4-methoxy or 3,4-dimethoxy, and ii) when m is 0, $R_3$ is $-COOC_2H_5$ and $R_4$ is $-NH_2$, n is not 0 and $-(R_1)_n$ is not 2-fluoro or 2-chloro.

DETAILED DESCRIPTION AND PREFERRED EMBODIMENTS

In the above formula (I), halo is, for example fluoro, chloro or bromo. A $C_1-C_4$ alkyl group includes, for example, methyl, ethyl, propyl and butyl, and is preferably methyl or ethyl. A $C_1-C_4$ alkoxy group is one such alkyl group linked through oxygen to an aryl nucleus, and a $C_{1-4}$ alkylthio is an alkyl group linked through sulphur. A hydroxyalkyl and hydroxyalkoxy are preferably of the formula $HO(CH_2)_x-$ and $HO(CH_2)_xO-$, respectively, where x is 1 to 4.

When n is 1 or 2 and there are one or two substituents on the naphtho nucleus, they can be at any of the positions 7 to 10, and when there are two substituents they can be the same or different. It is preferred that the naphtho nucleus is unsubstituted or that it bears a single substituent.

When $R_1$ is $-COOR_5$, $R_5$ is an ester group and is preferably $C_1-C_4$ alkyl, especially methyl or ethyl, and when $R_2$ is $-COOR_8$, $R_8$ is preferably $C_1-C_4$ alkyl, especially methyl or ethyl.

The group $R_3$ is preferably nitrile, but it can also be carboxy and $-COOR_{11}$ where $R_{11}$ is any ester group and is preferably $C_1-C_4$ alkyl, especially methyl or ethyl.

The group $R_4$ is preferably $-NH_2$. When $R_4$ is 1-pyrrolyl, it can be substituted by, for example, one or two $C_1-C_4$ alkyl, carboxy, hydroxy-$C_1-C_4$ alkyl or $-CHO$ groups.

A preferred group of compounds for use in the method of the invention is of formula (I) above wherein n and m are independently 0, 1, or 2; $R_1$ is halo, nitro, trifluoromethyl or $C_1-C_4$ alkoxy; $R_2$ is hydroxy, carboxyl or $C_1-C_4$ alkoxy and is attached at any of the positions 7, 8, 9, or 10; $R_3$ is nitrile; and $R_4$ is $NH_2$.

An especially preferred group of compounds for use in the method of the invention is of the formula

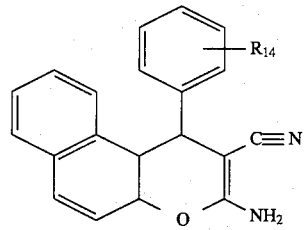

where $R_{14}$ is 3-nitro, 3-halo or 3-trifluoromethyl.

It will be appreciated that, when, for example $R_1$, $R_2$ or $R_3$ is $-COOH$, an opportunity exists for salts to be formed. They can be derived from any of the well known bases. Examples of base salts are those derived from ammonium hydroxide and alkali and alkaline earth metal hydroxides, carbonates and bicarbonates, as well as salts derived from aliphatic and aromatic amines, aliphatic diamines and hydroxy alkylamines. Bases especially useful in the preparation of such salts include ammonium hydroxide, potassium carbonate, sodium bicarbonate, lithium hydroxide, calcium hydroxide, methylamine, diethylamine, ethylene diamine, cyclohexylamine and ethanolamine. The potassium, sodium and lithium salt forms are particularly preferred.

In addition to pharmaceutically-acceptable salts, other salts are included in the invention. They may serve as intermediates in the purification of compounds or in the preparation of other, for example pharmaceutically-acceptable, acid addition salts, or are useful for identification, characterization or purification.

It will be appreciated that the compounds of the invention contain an asymmetric carbon atom which gives rise to enantiomers. The compounds are normally prepared as racemates and can conveniently be used as such, but individual enantiomers can be isolated by conventional techniques if so desired. Such racemates and individual enantiomers form part of the present invention.

The synthesis of certain phenyl-substituted naphtho [2,1-b] pyrans is described by Fathy Fahim Abdel-Latif in *Indian Journal of Chemistry*, 29B, 664–666, (1990), and Elagamey et al., *Collection Czechoslovak Chem. Commun.*, 53, 1534–1538, (1988), Sharanin et al., *Zhurnel Organicheskoi Khimii*, 18, 9, 2003–2005 (1982) and Klokol et al. *Zhurnal Organicheskoi Khimii* 23, 2, 412–421 (1987). No biological properties or activity are ascribed to the compounds disclosed.

The invention also comprises a process for producing a compound of formula (I) above, which comprises

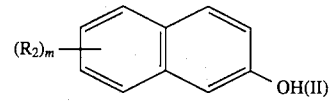

with a compound of the formula

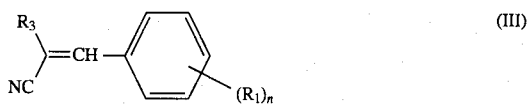

to give a compound of formula (I) in which $R_4$ is $-NH_2$, or (2) converting a compound of the formula

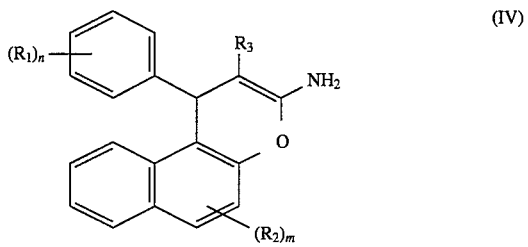

to a compound of formula (I) in which $R_4$ is $-NR_{12}R_{13}$, $-NR_{12}COR_{13}$, $-N(COR_{12})_2$, $-N=CHOCH_2R_{12}$, optionally substituted 1-pyrrolyl or

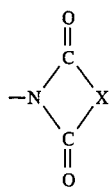

With regard to process (1), the reaction is preferably carried out at a temperature of from 0° C. to 100° C. and in the presence of an organic solvent, such as, for example, ethanol. Compounds of formula (II) are known or can be easily synthesized by known methods.

The reactants of formula (III) can be prepared by reacting the appropriate nitrile of the formula

$R_3CH_2CN$ with an aldehyde of the formula

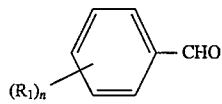

preferably at a temperature of from 20° C. to 100° C. in the presence of an organic base as catalyst such as piperidine and in the presence of an organic solvent, such as for example ethanol. The reactants of formula (III) need not be isolated but may be used directly in reaction of formula (II). The nitrile and aldehyde reactants are known compounds or can be made by methods known in the art.

With regard to process (2), the free enamine of formula (IV) can be prepared by reaction (1) and subsequently converted to compounds in which $R_4$ takes other values. For example, the free amino group can be alkylated with reagents of formula $R_{12}X$ or $R_{13}X$ where X is halogen, or $(R_{12})_2SO_4$ or $(R_{13})_2SO_4$ to give the mono- or di-alkylated product. Similarly the amino group can be acylated with an acyl halide or an acid anhydride such as $R_{12}COX$ or $(R_{12}CO)_2O$ to give compounds in which $R_4$ is $-NHCOR_{12}$ or $-N(COR_{12})_2$. Compounds in which $R_4$ is $-N=CHOCH_2R_{12}$ are prepared by reaction with the appropriate trialkyl orthoformate. When $R_4$ is 1-pyrrolyl, it can be prepared by reaction of the appropriate optionally substituted furan.

As previously indicated these compounds are useful for the treatment of diabetic complications. The activity of the compounds of the present invention was identified through in vitro studies using activated endothelial cells.

Retinal capillary endothelial cell cultures were initiated from bovine eyes using a modification of the procedure of Buzney et al., *Investigative Ophthalmology and Visual Sciences*, 24: 470–483. Bovine eyes were transported on ice from a local abattoir. Extraocular muscle was trimmed from the eye, and the eye bisected posterior to the ora serrata. The vitreous and anterior portion of the eye were discarded, and the neuro-retina was gently dissected from the posterior eyecup. The retinas from 20 cattle were pooled and homogenized (5 strokes of a Teflon/glass homogenizer) in Hank's saline. The homogenate was passed through a 350µ filter to remove large debris and a 210µ filter to remove large vessels. The microvessels were trapped on a 85µ filter. The microvessels were resuspended in Hank's saline and digested with 7.5 mg/ml bacterial collagenase (Boeringher Mannhelm, Indianapolis) in Hank's saline for 1 hour at 37° C. The cells were pelleted by centrifugation (100 xg, 10 min), resuspended in 5 ml Endothelial Growth Media (EGM, Clonetics) and seeded in a gelatin-coated T-25 flask. After 24 hours the cells were trypsinized and replated in a gelatin coated T225. At 7 days and again at 14 days the cultures were labeled with acetylated lipoproteins labeled with the fluorescent probe (1,1'-dioctadecyl-3,3,3,3,-tetramethyl-indocarbocyanine perchlorate). The endothelial cells were separated from contaminating cell types using a fluorescent cell sorter as described in Voyta et al., *J. Cell Biology.* 99: 2034–2040.

Retinal capillary endothelial cells were seeded into 96-well plates and grown to confluence ($10_5$ cells/well) in EGM containing 10% fetal bovine serum (FBS). The media was changed to Dubecco's Modified Eagle's Medium with 10% fetal bovine serum 24 hours prior to the assay. The cells were treated with 50 nM 4-b phorbol 12,13-dibutyrate (4-b PDBu) to activate PKC and produce the activated endothelial phenotype characteristic of the diabetic state. The activated cells were treated with a series of dilutions of the test compounds. The phorbol esters and the test compounds were dissolved in DMSO before adding to the culture media. The cultures were incubated at 37° C. for 48 hours. Following treatment, the cells were lysed with 25 mM $NH_4OH$ in 0.5% triton X-100.

The activation of bovine retinal capillary endothelial cells was monitored through alterations in cellular plasminogen activator (PA) activity in the cell lysates. Plasminogen activator activity was determined in a 50 µl aliquot of cell lysate using the synthetic substrate H-D-valyl-L-leucyl-lysine-p-nitroaniline dihydrochloride (Kabi).

Treatment of confluent bovine retinal capillary endothelial cells for 48 hours with PDBu resulted in a 12 fold increase in PA activity associated with the cell layer and a 12 fold increase in PA released into the media. There was also a two fold increase in cell number. This increase in activation occurred only after treatment with phorbol esters known to activate PKC (4-b PDBu, 4-b PHA, but not 4-a PDBu, 4-a PHA). No cleavage of the synthetic substrate was observed when plasminogen was omitted from the assay mixture, indicating that the increase in activity observed in phorbol treated cultures was restricted to activators of plasminogen. Dose-response curves generated for 4-b PDBu and 4-b PMA indicated $IC_{50}$ of 50 nH and 5 nH respectively. Elevated PA activity was observed only after prolonged (at least 8 hours) stimulation with phorbol esters. The PA activity continued to increase in a time and dose dependent manner for up to 72 hours, but constant stimulation with phorbol ester was required to maintain endothelial cell activation. Removal of the phorbol ester resulted in a rapid return of PA activity to normal levels.

Cell toxicity was determined in a parallel series of cultures using a neutral red assay. Borenfreund, E. and Puerner, J, *J. Tiss. Cult. Meth.* 9:7 (1984). The effectiveness of the present compounds to inhibit endothelial cell activation was found to be distinct from cell toxicity. In general, the compounds of the present invention were shown to be effective in inhibiting the endothelial cell activation induced by phorbol esters. Table 1 discloses the PA $ED_{50}$ value in this model for representative compounds. The in vitro endothelial cell model was correlated with in situ and in vivo activities by the following models.

The granulation tissue chamber model evaluates in situ the compound's ability to block the increase in blood flow and permeability induced by high glucose. In this model, circles of skin are removed from the backs of normal rats and stainless steel screw-cap chambers are mounted. New granulation tissue is formed within the chambers. Addition of 30–35 mM glucose (0.5 ml) twice daily to the chambers for 7 days induced a vascular dysfunction similar to that of diabetes—that is there is an increase in blood vessel permeability and an increase in blood flow. Blood flow is measured through the use of radiolabeled microspheres, and permeability is quantified using a dual label technique with iodinated albumin ($^{125}I/^{131}I$). Details of the model can be found in Tilton, et al., *Diabetes* 38: 1258–1270 and Williamson, et al., *J, Clin, Invest.* 85: 1167–1172. Representative compounds are dissolved in DMSO and diluted in a balanced salt solution to achieve a final concentration of 20 or 50 µM. The granulation chamber tissue is treated twice daily for 7 days to determine their effects on glucose-induced vascular dysfunction. Addition of 30–35 mM glucose to the granulation chamber induced a vascular dysfunction characterized by increased vessel permeability and increased blood flow.

The streptozotocin-induced diabetic rat model evaluates in vivo the compound's ability to block the microvascular dysfunction associated with streptozotocin-induced diabetes. Rats are made diabetic with an injection of streptozotocin, and the rats are fed ad libitum with a diet containing 0.1% of a representative compound. Blood flow is measured through the use of radiolabeled microspheres while permeability is quantified using a dual label technique with iodinated albumin ($^{125}I/^{131}I$). Details of the model can be found in Tilton et al., *Diabetes* 38: 1258–1270 and Williamson et at., *J. Clin. Invest.* 85: 1167– 1172.

Furthermore, compounds of the invention have been shown to inhibit vascular smooth cell proliferation. This has been demonstrated by using cultured smooth cells derived from rabbit aorta, proliferation being determined by the measurement of DNA synthesis. Cells are obtained by explant method as described in Ross, *J. Of Cell Bio.* 50: 172 (1971). Cells are plated in 96 well microtiter plates for five days. The cultures become confluent and growth arrested. The cells are then transferred to Dulbecco's Modified Eagle's Medium (DMEM) containing 0.5–2% platelet poor plasma, 2 mM L-glutamine, 100 U/ml penicillin, 100 µg ml streptomycin, 1 µ/ml $^3$H-thymidine, 20 ng/ml platelet-derived growth factor and varying concentrations of the compounds. Stock solution of compounds is prepared in dimethyl sulphoxide and then diluted to appropriate concentration (0.01–10 µg/ml) in the above assay medium. Cells are then incubated at 37° C. for 24 hours under 5% $CO_2$/95% air. At the end of 24 hours, the cells are fixed in methanol. $^3$H thymidine incorporation in DNA was then determined by scintillation counting as described in Bonin et al., *Exp. Cell Res.* 181:475–482 (1989).

Inhibition of smooth muscle cell proliferation by the compounds of the invention is further demonstrated by determining their effects on exponentially growing cells. Smooth muscle cells from rabbit aortae are seeded in 12 well tissue culture plates in DMEM containing 10% fetal bovine serum, 2 mM L-glutamine, 100 U/ml penicillin, and 100 µg/ml streptomycin. After 24 hours, the cells are attached, the medium is replaced with DMEM containing 2% platelet poor plasma, 2 mM L-glutamine, 100 U/ml penicillin, 100 µg/ml streptomycin, 40 ng/ml platelet-derived growth factor and indicated concentrations of the compounds. Cells are allowed to grow for four days. Cells are treated with trypsin and number of cells in each cultures is determined by counting using a ZM-Coulter counter.

Activity in the above tests indicates that the compounds of the invention are of potential in the treatment of restenosis. Table 1 discloses the $IC_{50}$ value of representative compounds tested in the $^3$H-thymidine incorporation model. Thus the invention specifically provides a method of treating restenosis, which comprises administering to a patient in need of treatment an effective amount of a compound of the formula (I).

The compounds may be administered by various routes, for example, by the oral or rectal route, topically or parenterally, for example by injection, being usually employed in the form of a pharmaceutical formulation. Such formulations form part of the present invention and are prepared in a manner well known in the pharmaceutical art and normally comprise at least one active compound in association with a pharmaceutically-acceptable diluent or carrier. In making the formulations of the present invention, the active ingredient will usually be mixed with a carrier, or diluted by a carrier, and/or enclosed with a carrier which may, for example, be in the form of a capsule, sachet, paper or other container. Where the carrier serves as a diluent, it may be solid, semi-solid, or liquid material which acts as a vehicle, excipient or medium for the active ingredient. Thus, the composition may be in the form of tablets, lozenges, sachets, cachets, elixirs, suspensions, as a solid or in a liquid medium, ointments containing, for example, up to 10% by weight of the active compound, soft and hard gelatin capsules, suppositories, injection solutions and suspensions and sterile packaged powders.

Some examples of suitable carriers are lactose, dextrose, sucrose, sorbitol, mannitol, starches, gum acacia, calcium phosphate, alginates, tragacanth, gelatin, syrup, methyl cellulose, methyl- and propyl-hydroxybenzoate, talc magnesium stearate and mineral oil. The formulations of the injection may, as is well known in the art, be formulated so as to provide quick, sustained or delayed release of the active ingredient after administration to the patient.

Where the formulations are in unit dosage form, it is preferred that each unit dosage form contains from 5 mg to 500 mg, for example, from 25 mg to 200 mg. The term 'unit dosage form' refers to physically discrete units suitable as unit dosages for human subjects and animals, each unit containing a predetermined quantity of active material calculated to produce the desired therapeutic effect, in association with the required pharmaceutical carrier.

The term "effective amount" as used herein, means an amount of a compound of the present invention which is capable of inhibiting, blocking, or reversing the activation or proliferation of cells. The activity contemplated by the present methods includes both medical therapeutic and/or prophylactic treatment, as appropriate. The specific dose of a compound administered according to this invention to obtain a therapeutic and/or prophylactic effects will, of course, be determined by the particular circumstances surrounding the case, including, for example, the compound administered, the route of administration, and the condition being treated.

The compounds are effective over a wide dosage range and, for example, dosages per day will normally fall within the range of from 0.5 to 300 mg/kg, more usually in the range of from 5 to 100 mg/kg. However, it will be understood that the effective amount administered will be determined by the physician in the light of the relevant circumstances including the condition to be treated, the choice of compound to be administered, and the chosen route of administration, and therefore the above dosage ranges are not intended to limit the scope of the invention in any way.

The term "treating" includes the administration of a compound of the present invention to prevent the onset of the symptoms, alleviating the symptoms, or eliminating the disease, condition or disorder.

In the treatment of restenosis, the administration of a compound of the invention may be local or systemic delivery. Systemic delivery includes techniques that introduce the compound to the entire organism. Examples of systemic delivery include oral and intravenous administration.

The local delivery of a compound of the invention may be by a variety of techniques which administer the compound at or near the proliferative site. Examples of local delivery techniques are not intended to be limiting but to be illustrative of the techniques available. Examples include local delivery catheters, site specific carriers, implants, or direct injection.

Local delivery by a catheter allows the administration of a pharmaceutical agent directly to the proliferative lesion. Examples of local delivery using a balloon catheter are described in EP 0 383 492 A2 and U.S. Pat. No. 4,636,195 (Wolinsky, 13th Jan. 1987).

Local delivery by an implant describes the surgical placement of a matrix that contains the pharmaceutical agent into the proliferative lesion. The implanted matrix releases the pharmaceutical agent by diffusion, chemical reaction, or solvent activators. Langer, *Science* 249:1527–1533 (September 1990). An example of local delivery by an implant is the use of a stent. Stents are designed to mechanically prevent the collapse and reocclusion of the coronary arteries. Incorporating a pharmaceutical agent into the stent delivers the drug directly to the proliferative site. Local delivery by this technique is described in Kohn, *Pharmaceutical Technology* (October 1990). A second example is a delivery system in which a polymer that contains the pharmaceutical agent is injected into the lesion in liquid form. The polymer then cures to form the implant in situ. This technique is described in PCT WO 90/03768 (Donn, 19th Apr. 1990). Another example is the delivery of a pharmaceutical agent by polymeric endoluminal sealing. This technique uses a catheter to apply a polymeric implant to the interior surface of the lumen. The pharmaceutical agent incorporated into the biodegradable polymer implant is thereby released at the surgical site. It is described in PCT WO 90/01969 (Schindler, 23 Aug. 1989). A final example of local delivery by an implant is by direct injection of vesicles or microparticulates into the proliferative site. These microparticulates may be composed of substances such as proteins, lipids, carbohydrates or synthetic polymers. These microparticulates have the pharmaceutical agent incorporated throughout the microparticle or over the microparticle as a coating. Delivery systems incorporating microparticulates are described in Lange, *Science* 249: 1527–1533 (September 1990) and Mathiowitz, et al., *J. App. Poly. Sci.*, 26:809 (1981).

Local delivery by site specific carriers describes attaching the pharmaceutical agent to a carrier which will direct or link the drug to the proliferative cells. Examples of this delivery technique include the use of carriers such as a protein ligand or a monoclonal antibody or a membrane anchored linker. Lange, *Science* 249:1527–1533 (September 1990); Langworth, *Genetic Engineering News* (September 1990).

Local delivery by direct injection describes injecting fine particles of the compound suspended in an inert carrier such as sterile saline solution directly into the proliferative region.

The examples of local delivery are merely illustrative and are not mutually exclusive. For example, the delivery of microparticles to the proliferative smooth muscle cells may be by a local delivery catheter or direct injection.

The dosage of a compound of the invention for treatment of restenosis is dependent upon the method of administration and the particular circumstances of the patient. An effective amount is an amount sufficient to inhibit the migration and proliferation of vascular smooth muscle cells. The preferred dosage range is defined to be about 1 μg/day to about 500,000 μg/day delivered at or near the proliferative site.

The preparation of representative compounds of the present invention is illustrated by the following preparations and Examples.

PREPARATION

2-Fluorobenzylidenemalonitrile

2-Fluorobenzaldehyde (15.8 ml) was dissolved in ethanol (100 ml) and to the stirred solution was added malonitrile (9.9 g). The solution was heated to reflux, the heating discontinued and piperidine (4 drops) was added. Once the vigorous reaction had diminished, the solution was heated for 15 minutes and then chilled. Crystals of product were filtered off and washed with ethanol, m.p. 122° C.

EXAMPLE 1

2-Amino-4-(3-nitrophenyl)-4H-naphtho[2,1-b]pyran-3-carbonitrile

3-Nitrobenzaldehyde (7.6 g) and malononitrile (3.3 g) were dissolved in ethanol (40 ml) by heating under reflux. Once crystals of intermediate 3-nitrobenzylidenemalononitrile were apparent, 2-naphthol (7.2 g) was added, followed by piperidine (5 ml). The solution was heated for one hour and then left to stir at ambient temperature for 24 hours. The solid was filtered off, washed with ethanol and dried, m.p. 237° C.

EXAMPLE 2

2-Amino-4-(3-nitrophenyl) -4H-naphtho[2, 1-b]pyran-3-carbonitrile

2-Naphthol (3.3 g) was dissolved in ethanol (44 ml) with stirring. 3-Nitrobenzylidenemalononitrile (4.5 g) was added, followed by pipermaline (2.3 ml). The solution was stirred at ambient temperature for 45 minutes, and a solid deposited during this time. The product was filtered off and washed with ethanol. Recrystallization from isopropanol gave cream crystals, m.p. 238°–241° C.

Similarly prepared were:

EXAMPLE 3

2-Amino-4-(4-nitrophenyl)-4H-naphtho[2,1-b]pyran-3-carbonitrile, m.p. 170°–172° C.

EXAMPLE 4

2-Amino-4-(2-nitrophenyl)-4H-naphtho[2,1-b]pyran-3-carbonitrile, m.p. 284.5°–286° C.

EXAMPLE 5

2-Amino-4-(3-bromophenyl)-4H-naphtho[2,1-b]pyran-3-carbonitrile, m.p. 222°–224° C.

EXAMPLE 6

2-Amino-4-(3-chlorophenyl)-4H-naphtho[2,1-b]pyran-3-carbonitrile, m.p. 237.5°–239° C.

EXAMPLE 7

2-Amino-4-(3-fluorophenyl)-4H-naphtho[2,1-b]pyran-3-carbonitrile, m.p. 272.5°–274° C.

EXAMPLE 8

2-Amino-4-(4-fluorophenyl)-4H-naphtho[2,1-b]pyran-3-carbonitrile, m.p. 230°–232.5° C.

EXAMPLE 9

2-Amino-4-(2-fluorophenyl) -4H-naphtho[2,1-b]pyran-3-carbonitrile, m.p. 292°–294.5° C.

EXAMPLE 10

2-Amino-4-[3-(trifluoromethyl)phenyl]-4H-naphtho[2,1-b] pyran-3-carbonitrile, m.p. 197°–199° C.

EXAMPLE 11

2-Amino-3-cyano-4-(3-nitrophenyl)-4H-naphtho[2,1-b]pyran-7-carboxylic acid, m.p. >295° C.

EXAMPLE 12

2-Amino-10-hydroxy-4-(3-nitrophenyl)-4H-naphtho[2,1-b] pyran-3-carbonitrile, m.p. 248°–250° C. (from 2,3-naphthalene diol)

EXAMPLE 13

2-Amino-6-methoxy-4-(3-nitrophenyl)-4H-naphtho[2,1-b]pyran- 3-carbonitrile, m.p. 251°–252.5° C. (from 7-methoxy-2-naphthol)

EXAMPLE 14

2-Amino-3-cyano-4-(3-methoxyphenyl)-4H-naphtho[2,1-b]pyran- 7-carboxylic acid, m.p. >300° C. (from 6-hydroxy-2-naphthoic acid)

EXAMPLE 15

2-Amino-3-cyano-4-(3-carboxyphenyl)-4H-naphtho[2,1-b]pyran- 7-carboxylic acid, m.p. >260° C. (from 6-hydroxy-2-naphthoic acid)

EXAMPLE 16

2-Amino-3-cyano-4-[3-(trifluoromethoxy)phenyl]-4H-naphtho[ 2,1-b]pyran-7-carboxylic acid, m.p. 263°–266° C. (from 6-hydroxy-2-naphthoic acid)

EXAMPLE 17

Ethyl 3-cyano-2-ethoxymethyleneamino-4-(3-nitrophenyl)-4H-naphtho[ 2,1-b]pyran-7-carboxylate 2-Amino-3-cyano-4-(3-nitrophenyl)-4H-naphtho [ 2,1-b] pyran-7-carboxylic acid (3.26 g) was suspended magnetically in triethyl orthoformate (40 ml) and brought to reflux temperature. After a few hours at this temperature a fraction coming over at 80°–120° C. was distilled off. More triethyl orthoformate (20 ml) was added and the refluxing was continued for 18 to 24 hours. The solution was evaporated to dryness, and the residue was triturated with methanol and recrystallized from ethyl acetate to give white crystals, m.p. 187.5°–189.5° C.

The following formulations illustrate the invention:

EXAMPLE 18

Soft gelatin capsule

Each soft gelatin capsule contains:

| | |
|---|---|
| Active ingredient | 150 mg |
| Arachis oil | 150 mg |

After mixing together, the blend is filled into soft gelatin capsules using the appropriate equipment.

EXAMPLE 19

Hard gelatin Capsule

Each capsule contains:

| | |
|---|---|
| Active ingredient | 50 mg |
| PEG 4000 | 250 mg |

The PEG 4000 is melted and mixed with the active ingredient. While still molten, the mixture is filled into capsule shells and allowed to cool.

EXAMPLE 20

Tablets each containing 10 mg of active ingredient are made up as follows:

| | |
|---|---|
| Active ingredient | 10 mg |
| Starch | 160 mg |
| Microcrystalline cellulose | 100 mg |
| Polyvinylpyrrolidone (as 10% solution in water) | 13 mg |
| Sodium carboxymethyl starch | 14 mg |
| Magnesium stearate | 3 mg |
| Total | 300 mg |

The active ingredient, starch and cellulose are mixed thoroughly. The solution of polyvinylpyrrolidone is mixed with the resultant powders and passed through a sieve. The granules so produced are dried and re-passed through a sieve. The sodium carboxymethyl starch and magnesium stearate are then added to the granules which, after mixing, are compressed in a tablet machine to yield tablets each weighing 300 mg.

EXAMPLE 21

Capsules each containing 20 mg of medicament are made as follows:

| | |
|---|---|
| Active ingredient | 20 mg |
| Dried starch | 178 mg |
| Magnesium stearate | 2 mg |
| Total | 200 mg |

TABLE 1

| Example | PA ED$_{50}$ (μM) | $^3$H-Thymidine IC$_{50}$ (μM) |
| --- | --- | --- |
| 2 | 0.7 | 2.5 |
| 3 | >20 | 8.0 |
| 4 | >20 | >30 |
| 5 | 0.7 | 1.8 |
| 6 | 1 | 2.0 |
| 7 | * | 2.0 |
| 8 | 9 | 1.5 |
| 9 | >20 | >3.0 |
| 10 | 0.05 | 0.5 |
| 11 | >20 | >30 |
| 12 | 0.65 | 3.0 |
| 13 | >20 | >3.0 |
| 14 | >100 | * |
| 15 | 5.0 | * |
| 16 | >100 | * |
| 17 | 8 | 6.0 |

*indicates data are not available

We claim:

1. A method of treating diabetic complications, which comprises administering to a patient in need of treatment an effective amount of a compound of the Formula I:

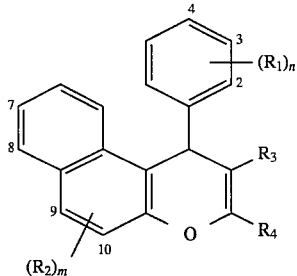

(I)

wherein n and m are independently 0, 1 or 2;

$R_1$ is halo, trifluoromethyl, $C_1$-$C_4$ alkoxy, hydroxy, nitro, $C_1$-$C_4$ alkyl, $C_1$-$C_4$ alkylthio, hydroxy-$C_1$-$C_4$ alkyl, hydroxy-$C_1$-$C_4$ alkoxy, trifluoromethoxy, carboxy, —COOR$_5$ where R$_5$ is a $C_1$-$C_4$ alkyl, —COR$_6$, —CONR$_6$R$_7$ or —NR$_6$R$_7$ where R$_6$ and R$_7$ are each hydrogen or $C_1$-$C_4$ alkyl;

$R_2$ is halo, trifluoromethyl, $C_1$-$C_4$ alkoxy, hydroxy, nitro, $C_1$-$C_4$ alkyl, $C_1$-$C_4$ alkylthio, hydroxy-$C_1$-$C_4$ alkyl, hydroxy-$C_1$-$C_4$ alkoxy, trifluoromethoxy, carboxy, —COOR$_8$ where R$_8$ is a $C_1$-$C_4$ alkyl, —COR$_9$, —CONR$_9$R$_{10}$ or —NR$_9$R$_{10}$ where R$_9$ and R$_{10}$ are each hydrogen or $C_1$-$C_4$ alkyl;

$R_3$ is nitrile, carboxy or —COOR$_{11}$ where R$_{11}$ is a $C_1$-$C_4$ alkyl; and $R_4$ is —NR$_{12}$R$_{13}$, —NR$_{12}$COR$_{13}$, —N(COR$_{12}$)$_2$, —N=CHOCH$_2$R$_{12}$,

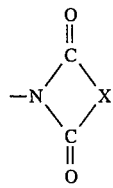

or 1-pyrrolyl; wherein R$_{12}$ and R$_{13}$ are each hydrogen or $C_1$-$C_4$ alkyl; X is $C_2$-$C_4$ alkylene;

wherein 1-pyrrolyl is optionally substituted with one or two moieties selected from the group consisting of $C_1$-$C_4$ alkyl, carboxy, hydroxy-$C_1$-$C_4$ alkyl, or —CHO;

or a pharmaceutically-acceptable salt thereof.

2. A method according to claim 1 wherein the compound of Formula I is one in which n and m are independently 0, 1 or 2;

$R_1$ is halo, nitro, trifluoromethyl or $C_1$-$C_4$ alkoxy;

$R_2$ is hydroxy, carboxy or $C_1$-$C_4$ alkoxy.

3. A method of inhibiting endothelial cell activation, which comprises administering to a patient in need of treatment an effective amount of a compound of the Formula I:

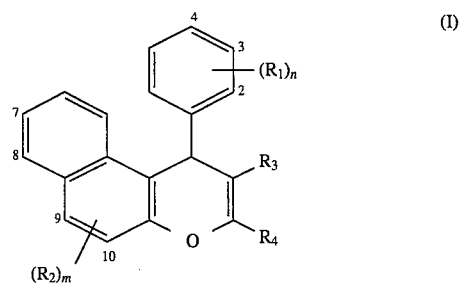

(I)

wherein n and m are independently 0, 1 or 2;

$R_1$ is halo, trifluoromethyl, $C_1$-$C_4$ alkoxy, hydroxy, nitro, $C_1$-$C_4$ alkyl, $C_1$-$C_4$ alkylthio, hydroxy-$C_1$-$C_4$ alkyl, hydroxy-$C_1$-$C_4$ alkoxy, trifluoromethoxy, carboxy, —COOR$_5$ where R$_5$ is a $C_1$-$C_4$ alkyl, —COR$_6$, —CONR$_6$R$_7$ or —NR$_6$R$_7$ where R$_6$ and R$_7$ are each hydrogen or $C_1$-$C_4$ alkyl;

$R_2$ is halo, trifluoromethyl, $C_1$-$C_4$ alkoxy, hydroxy, nitro, $C_1$-$C_4$ alkyl, $C_1$-$C_4$ alkylthio, hydroxy-$C_1$-$C_4$ alkyl, hydroxy-$C_1$-$C_4$ alkoxy, trifluoromethoxy, carboxy, —COOR$_8$ where R$_8$ is a $C_1$-$C_4$ alkyl, —COR$_9$, —CONR$_9$R$_{10}$ or —NR$_9$R$_{10}$ where R$_9$ and R$_{10}$ are each hydrogen or $C_1$-$C_4$ alkyl;

$R_3$ is nitrile, carboxy or —COOR$_{11}$ where R$_{11}$ is a $C_1$-$C_4$ alkyl; and $R_4$ is —NR$_{12}$R$_{13}$, —NR$_{12}$COR$_{13}$, —N(COR$_{12}$)$_2$, —N=CHOCH$_2$R$_{12}$,

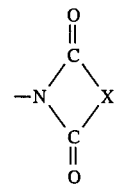

or 1-pyrrolyl; wherein R$_{12}$ and R$_{13}$ are each hydrogen or $C_1$-$C_4$ alkyl; X is $C_2$-$C_4$ alkylene;

wherein 1-pyrrolyl is optionally substituted with one or two moieties selected from the group consisting of $C_1$-$C_4$ alkyl, carboxy, hydroxy-$C_1$-$C_4$ alkyl, or —CHO;

or a pharmaceutically-acceptable salt thereof.

4. A method of treating vascular dysfunction, which comprises administering to a patient in need of treatment an effective amount of a compound of the Formula I:

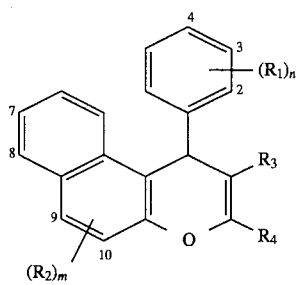 (I)

wherein n and m are independently 0, 1 or 2;

$R_1$ is halo, trifluoromethyl, $C_1$–$C_4$ alkoxy, hydroxy, nitro, $C_1$–$C_4$ alkyl, $C_1$–$C_4$ alkylthio, hydroxy-$C_1$–$C_4$ alkyl, hydroxy-$C_1$–$C_4$ alkoxy, trifluoromethoxy, carboxy, —$COOR_5$ where $R_5$ is a $C_1$–$C_4$ alkyl, —$COR_6$, —$CONR_6R_7$ or —$NR_6R_7$ where $R_6$ and $R_7$ are each hydrogen or $C_1$–$C_4$ alkyl;

$R_2$ is halo, trifluoromethyl, $C_1$–$C_4$ alkoxy, hydroxy, nitro, $C_1$–$C_4$ alkyl, $C_1$–$C_4$ alkylthio, hydroxy-$C_1$–$C_4$ alkyl, hydroxy-$C_1$–$C_4$ alkoxy, trifluoromethoxy, carboxy, —$COOR_8$ where $R_8$ is a $C_1$–$C_4$ alkyl, —$COR_9$, —$CONR_9R_{10}$ or —$NR_9R_{10}$ where $R_9$ and $R_{10}$ are each hydrogen or $C_1$–$C_4$ alkyl;

$R_3$ is nitrile, carboxy or —$COOR_{11}$ where $R_{11}$ is a $C_1$–$C_4$ alkyl; and $R_4$ is —$NR_{12}R_{13}$, —$NR_{12}COR_{13}$, —$N(COR_{12})_2$, —N=CHOCH$_2$R$_{12}$,

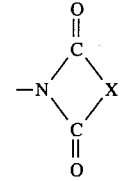

or 1-pyrrolyl; wherein $R_{12}$ and $R_{13}$ are each hydrogen or $C_1$–$C_4$ alkyl; X is $C_2$–$C_4$ alkylene;

wherein 1-pyrrolyl is optionally substituted with one or two moieties selected from the group consisting of $C_1$–$C_4$ alkyl, carboxy, hydroxy-$C_1$–$C_4$ alkyl, or —CHO;

or a pharmaceutically-acceptable salt thereof.

* * * * *

UNITED STATES PATENT AND TRADEMARK OFFICE
CERTIFICATE OF CORRECTION

PATENT NO. : 5,514,706
DATED : May 7, 1996
INVENTOR(S) : Ambler et al.

It is certified that error appears in the above-indentified patent and that said Letters Patent is hereby corrected as shown below:

Column 2, lines 55-56 reads "-COORS..." should read ---COOR$_5$--.

Column 2, lines 61-62 reads "-COORS..." should read ---COOR$_8$--.

Column 4, line 5 reads " 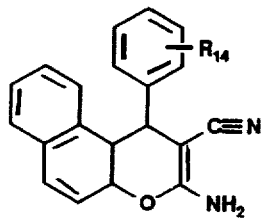 ..." should read -- 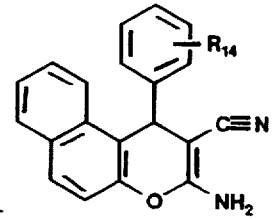 --.

Column 4, line 49 reads "Zhurnel..." should read --Zhurnal--.

Column 4, lines 55-56 reads "(I) above, which comprises..." should read --(I) above, which comprises
   (1) reacting a compound of formula--.

Column 6, line 25 reads "(10$_5$ cells/well)..." should read --(10$^5$ cells/well)--.

Column 6, line 50 reads "PHA..." should read --PMA--.

UNITED STATES PATENT AND TRADEMARK OFFICE
CERTIFICATE OF CORRECTION

PATENT NO. : 5,514,706
DATED : May 7, 1996
INVENTOR(S) : Ambler et al.

It is certified that error appears in the above-indentified patent and that said Letters Patent is hereby corrected as shown below:

Column 6, line 51 reads "PHA..." should read --PMA--.

Column 6, line 56 reads "50 nH and 5 nH..." should read --50 nM and 5 nM--.

Column 10, line 48 reads "-4H-naphtho[2, 1-b]pyran-3-..." should read ---4H-naphtho[2,1-b]pyran-3-

Column 10, line 52 reads "pipermaline..." should read --piperidine--.

Signed and Sealed this

Eighteenth Day of February, 1997

Attest:

BRUCE LEHMAN

*Attesting Officer*  *Commissioner of Patents and Trademarks*